United States Patent [19]
Willard et al.

[11] Patent Number: 5,219,335
[45] Date of Patent: Jun. 15, 1993

[54] INTRAVASCULAR DEVICE SUCH AS INTRODUCER SHEATH OR BALLOON CATHETER OR THE LIKE AND METHODS FOR USE THEREOF

[75] Inventors: Lloyd Willard, Miltona; Wayne Sieben, Alexandria, both of Minn.

[73] Assignee: Scimed Life Systems, Inc., Maple Grove, Minn.

[21] Appl. No.: 809,715

[22] Filed: Dec. 18, 1991

Related U.S. Application Data

[63] Continuation-in-part of Ser. No. 704,828, May 23, 1991, abandoned.

[51] Int. Cl.$^5$ .................. A61M 5/00; A61M 25/00
[52] U.S. Cl. ..................... 604/164; 604/43; 604/96
[58] Field of Search .......... 604/43, 164, 280, 284, 604/173, 96-102

[56] References Cited

U.S. PATENT DOCUMENTS

| | | | |
|---|---|---|---|
| 3,670,729 | 6/1972 | Bennett et al. | 604/164 |
| 3,769,981 | 11/1973 | McWhorter. | |
| 3,915,168 | 11/1975 | Monestere, Jr. | 604/164 |
| 4,033,331 | 7/1977 | Guss et al. . | |
| 4,052,989 | 11/1977 | Kline | 604/164 |
| 4,270,535 | 6/1981 | Bogue et al. | 604/164 |
| 4,367,740 | 1/1983 | Evanoski, III | 604/43 |
| 4,450,402 | 9/1985 | Aigner | 604/44 |
| 4,552,554 | 11/1985 | Gould et al. . | |
| 4,577,637 | 3/1986 | Mueller, Jr. . | |
| 4,601,701 | 7/1986 | Mueller, Jr. . | |
| 4,619,643 | 10/1986 | Bai | 604/43 |
| 4,661,110 | 4/1987 | Fortier et al. | 604/284 |
| 4,769,005 | 9/1988 | Ginsburg et al. . | |
| 4,787,892 | 11/1988 | Rosenberg | 604/164 |
| 4,798,193 | 1/1989 | Giesy et al. . | |
| 4,824,435 | 4/1989 | Giesy et al. . | |
| 4,834,102 | 5/1989 | Schwarzchild et al. | 128/662.06 |
| 4,922,924 | 5/1990 | Gambale et al. | 604/164 |
| 4,928,693 | 5/1990 | Goodin et al. . | |
| 4,932,413 | 6/1990 | Shockey et al. | 604/164 |
| 4,955,863 | 9/1990 | Walker et al. | 604/164 |
| 4,957,484 | 9/1990 | Murtfeldt | 604/164 |
| 4,976,689 | 12/1990 | Buchbinder et al. | 604/164 |
| 4,998,919 | 3/1991 | Schnepp-Pesch | 604/164 |
| 5,009,636 | 4/1991 | Wortley et al. | 604/43 |
| 5,029,580 | 7/1991 | Radford et al. | 604/43 |
| 5,053,023 | 10/1991 | Martin | 604/43 |
| 5,057,073 | 10/1991 | Martin . | |

FOREIGN PATENT DOCUMENTS

| | | |
|---|---|---|
| 0093887 | 11/1983 | European Pat. Off. . |
| 0132215 | 5/1984 | European Pat. Off. . |
| 0380102 | 8/1990 | European Pat. Off. . |
| 2644020 | 4/1978 | Fed. Rep. of Germany . |
| 2929562 | 1/1980 | Fed. Rep. of Germany . |
| WO92/11055 | 7/1992 | PCT Int'l Appl. . |

Primary Examiner—Paul J. Hirsch
Attorney, Agent, or Firm—Willian Brinks Olds Hofer Gilson & Lione

[57] ABSTRACT

An intravascular device such as an introducer sheath or a balloon catheter, and methods for use thereof, comprising an elongate member having a proximal end and a distal end and a first lumen and a second lumen. The first lumen communicates with a first proximal opening at the proximal end of the elongate member and with a distal opening at the distal end of the elongate member. The second lumen terminates distally and communicates with the first lumen at a location proximal of the first distal opening and has a proximal opening located proximally therefrom. One or more perfusion openings may be located in the device to allow blood flow therethrough. The proximal opening of the second lumen may be located distally of the proximal opening of the first lumen. A balloon may be located on a distal portion of the elongate shaft.

29 Claims, 5 Drawing Sheets

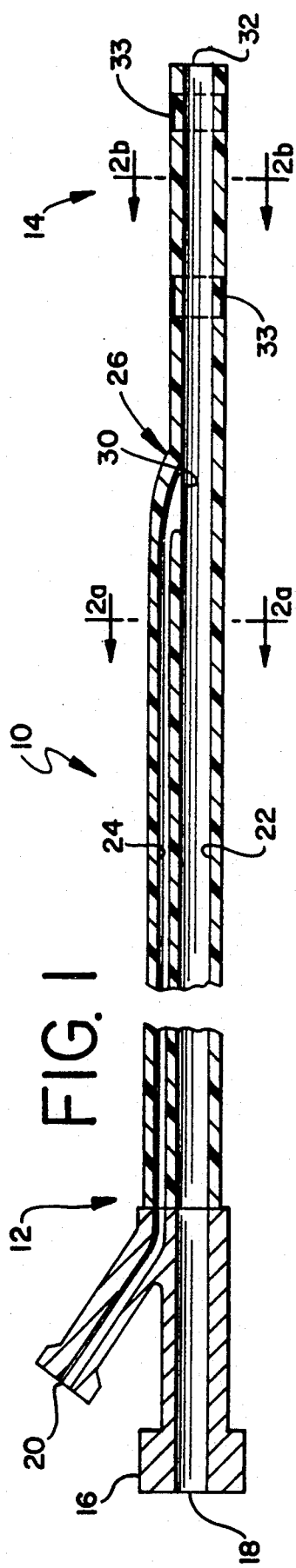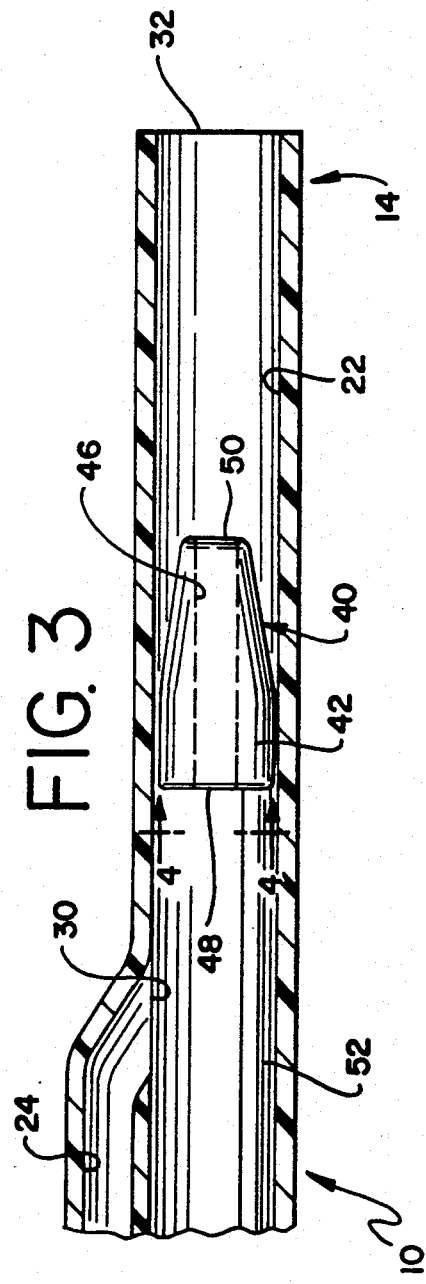

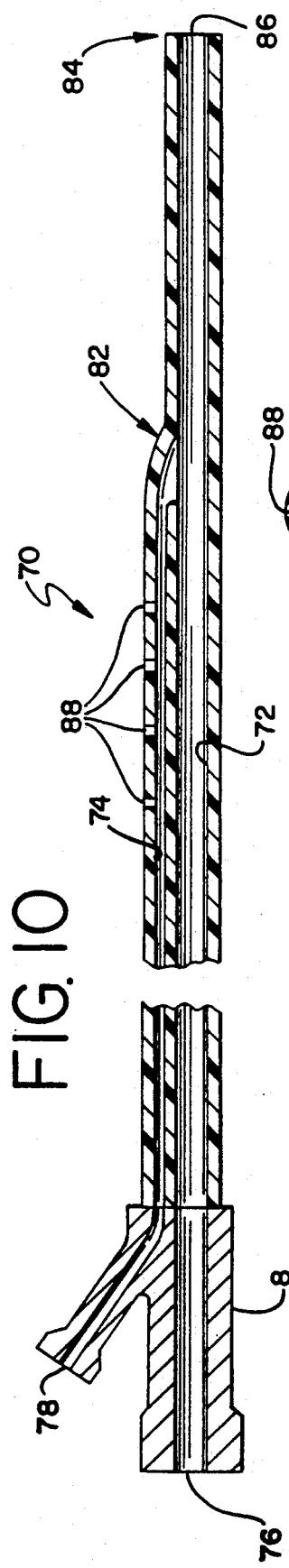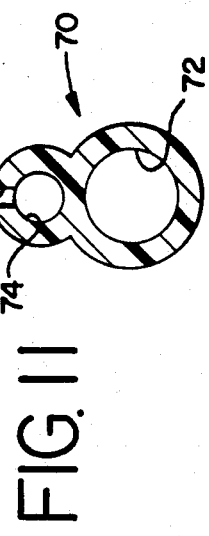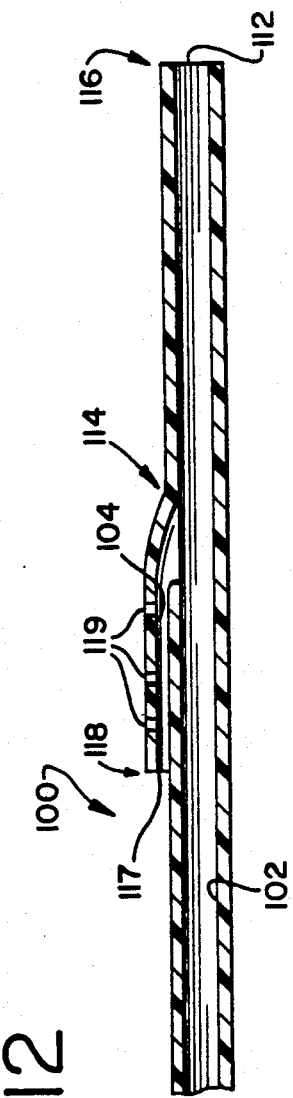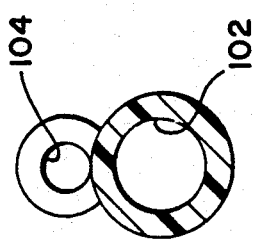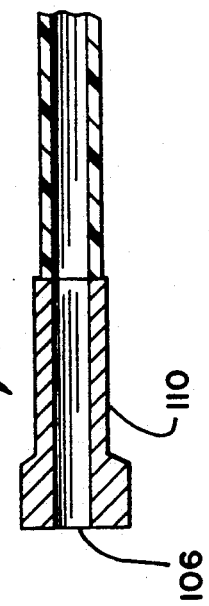

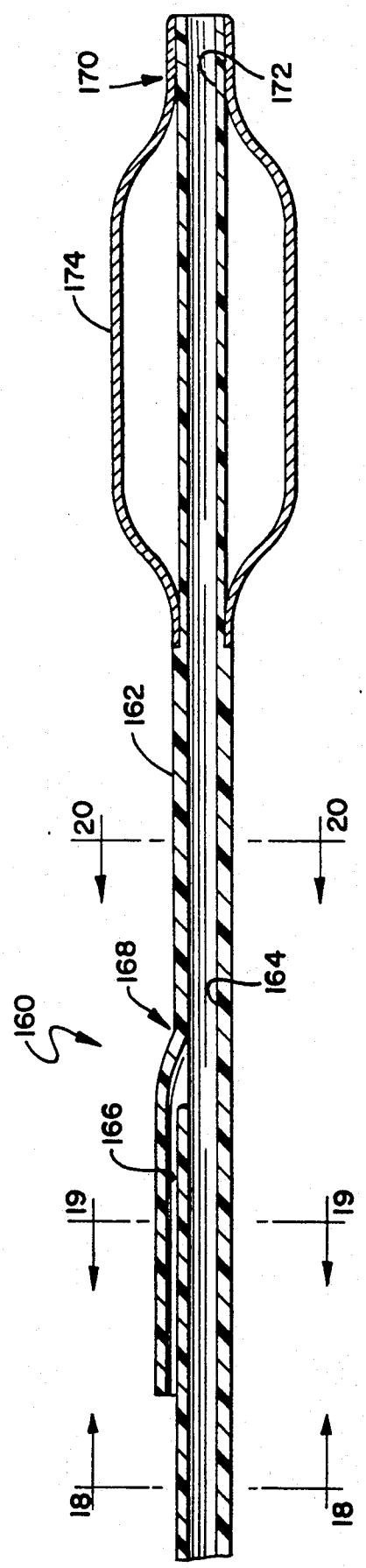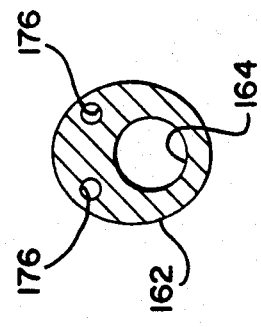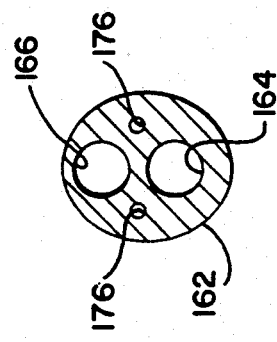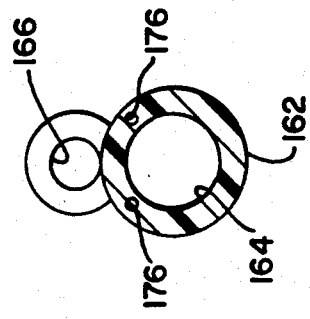

INTRAVASCULAR DEVICE SUCH AS INTRODUCER SHEATH OR BALLOON CATHETER OR THE LIKE AND METHODS FOR USE THEREOF

REFERENCE TO RELATED APPLICATIONS

This application is a continuation in part of Ser. No. 07/704,828, filed May 23, 1991 now abandoned.

BACKGROUND OF THE INVENTION

The present invention relates to intravascular devices and in particular to an intravascular device such as an improved introducer sheath used for positioning a catheter, imager, or other device in the vascular system of a patient or an intravascular device such as a balloon catheter with a new design and construction.

Various therapies have been developed for treating vascular disease or other conditions that occlude or reduce the lumen size of portions of the vascular system. Such therapeutic techniques include angioplasty, atherectomy, laser irradiation, and so on. Diagnostic techniques have been developed to measure or image the extent of an occlusion of a vessel, (e.g. stenosis). Such diagnostic techniques include ultrasonic imaging, Doppler measurements, and so on. These therapies and diagnostic techniques have achieved acceptance because of their effectiveness as well as the fact that they can be performed through a minor surgical procedure that is relatively non-disruptive to the patient.

Therapeutic and diagnostic procedures, such as those described above, rely on the positioning of a device into the vascular system of a patient via an incision at a location remote from the site of the stenosis, such as the femoral artery. Because each of the aforementioned therapies and diagnostic procedures relies upon positioning a device in the affected area, an important defining factor limiting the effective deployment of any of these devices is how small the device can be made. It is often in vessels of small inner diameters or tortuous passage ways that stenosis occurs. Thus, it is often preferable to make such therapeutic and diagnostic devices as small as possible to fit into remote coronary sites or other vessel locations where the vessel lumen inner diameters are very small.

Some therapeutic and diagnostic devices include their own guide wires located at the distal ends thereof to facilitate positioning in remote vessel locations. Other devices use an over-the-wire approach in which a central lumen of the device can accommodate a guide wire that is movable in relation to the device to facilitate positioning the device in a remote vessel location. Both of these approaches are very useful and are widely used. However, when such therapeutic or diagnostic devices are adapted with a positioning feature, such as a guide wire tip or a central lumen, the addition of such a positioning feature can increase the size of the device somewhat, thereby establishing a limitation on the size of a vessel into which it can be deployed that is larger than if such an additional feature were omitted.

Introducer sheaths have been employed to facilitate positioning therapeutic and diagnostic devices in remote regions of the vascular system. An introducer sheath can be a catheter-like device In a typical prior introducer sheath, the distal end of the introducer sheath is positioned inside of the guide catheter close to the desired site and the therapeutic or diagnostic device is inserted through the lumen of the introducer sheath out the distal end thereof into the vessel location The introducer sheath also provides the advantage that it can support the therapeutic or diagnostic device over all but the most distal end thereof. Introducer sheaths may be positioned by a guide wire that is first inserted through the lumen of the introducer sheath and then withdrawn to allow placement of the therapeutic or diagnostic device to be installed into the lumen.

A disadvantage of using such a prior introducer sheath is that if it is necessary to reposition the therapeutic or diagnostic device, the introducer sheath may also have to be repositioned. Repositioning of the introducer sheath may require withdrawing the therapeutic or diagnostic device, installing a guide wire into the lumen of the introducer sheath, positioning the guide wire past the distal end of the introducer sheath to the desired location, repositioning the introducer sheath, withdrawing the guide wire, and reintroducing the therapeutic or diagnostic device. This can be a time consuming and tedious process.

Accordingly, it is an object of the present invention to provide an introducer sheath that facilitates use and placement of devices in a vessel of a patient.

It is another object of the present invention to provide an introducer sheath that permits use in remote, distal portions of patient's vasculature.

SUMMARY OF THE INVENTION

According to a first aspect of the invention, there is provided an intravascular device such as an introducer sheath or a balloon catheter, and methods for use thereof, comprising an elongate member having a proximal end and a distal end and a first lumen and a second lumen. The first lumen communicates with a first proximal opening at the proximal end of the elongate member and with a distal opening at the distal end of the elongate member. The second lumen terminates distally and communicates with the first lumen at a location proximal of the first distal opening and has a proximal opening located proximally therefrom. One or more perfusion openings may be located in the device to allow blood flow therethrough. The proximal opening of the second lumen may be located distally of the proximal opening of the first lumen. A balloon may be located on a distal portion of the elongate shaft.

BRIEF DESCRIPTION OF THE DRAWINGS

FIG. 1 shows a first embodiment of the present invention.

FIG. 2a shows a cross section of the embodiment of FIG. 1 along line 2a—2a'

FIG. 2b shows a cross section of the embodiment of FIG. 1 along line 2b—2b',

FIG. 3 shows another embodiment of the present invention.

FIG. 4 shows a cross section of the embodiment of FIG. 3 along line 4—4'.

FIG. 10 shows another embodiment of the present invention.

FIG. 11 is a cross section corresponding to line 11—11' of FIG. 10.

FIG. 12 shows another embodiment of the present invention.

FIG. 13 is a cross section corresponding to line 13—13' of FIG. 12.

FIG. 17 shows another embodiment of the present invention.

FIG. 18 is a cross section corresponding to line 18—18' of FIG. 17.

FIG. 19 is a cross section corresponding to line 19—19' of FIG. 17.

FIG. 20 is a cross section corresponding to line 20—20' of FIG. 17.

DETAILED DESCRIPTION OF THE PRESENTLY PREFERRED EMBODIMENTS

Figure 5:
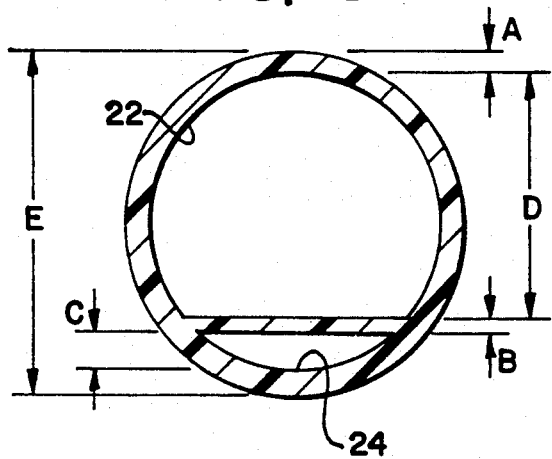
FIG. 5 shows a cross section corresponding to line 4—4' of FIG. 3 of an alternative embodiment
Figure 6:
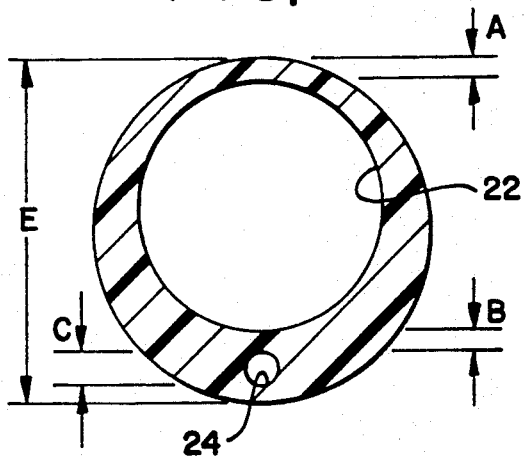
FIG. 6 shows a cross section corresponding to line 4—4' of FIG. 3 of an alternative embodiment.
Figure 7:
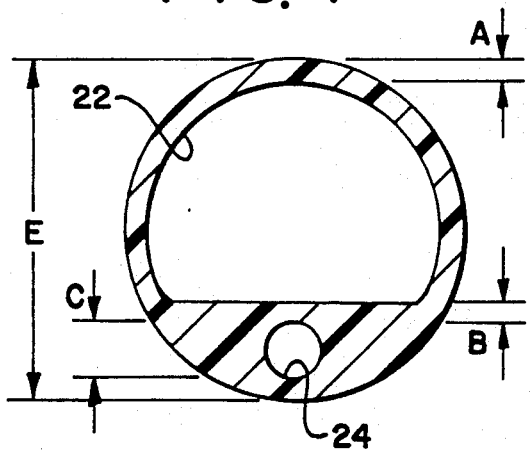
FIG. 7 shows a cross section corresponding to line 4—4' of FIG. 3 of an alternative embodiment.
Figure 8:
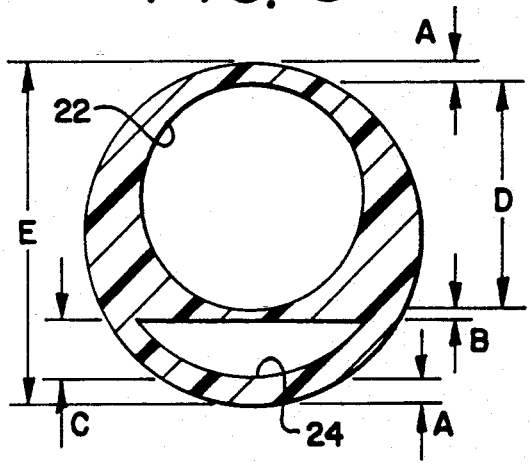
FIG. 8 shows a cross section corresponding to 4—4' of FIG. 3 of an alternative embodiment.

Referring to FIG. 1 there is depicted a first preferred embodiment of the present invention. This embodiment is an introducer sheath 10. The introducer sheath 10 has a proximal end 12 and a distal end 14. In one embodiment, the introducer sheath 10 is approximately 130 cm in length although other lengths may be used where appropriate. The introducer sheath 10 is used to position devices into the vascular system of a patient.

At the proximal end of the introducer sheath is a manifold 16. The manifold has two ports or openings: a main port 18 and an auxiliary port 20. The main port 18 communicates with a first or main lumen 22 of the introducer sheath and the auxiliary port 20 communicates with a second or auxiliary lumen 24 of the introducer sheath. The main lumen 22 and the auxiliary lumen 24 are positioned adjacent to each other and extend parallel to each other distally from the proximal end 12 of the introducer sheath. The outside walls of the main and auxiliary lumens are connected together, as shown in FIG. 2a, so as to form an integral elongate catheter-like member. The main and auxiliary lumens may be of the same size or may be of different sizes. In one preferred embodiment, the main lumen 22 has an inside diameter of 0.035 to 0.050 inches and the auxiliary lumen has an inside diameter of 0.018 to 0.021 inches. The outside dimension of the introducer sheath 10 in this section is approximately 0.065 to 0.086 inches.

The main and auxiliary lumens extend parallel to each other to a junction location 26. The junction location 26 is proximate of the distal end 14 of the introducer sheath. In a preferred embodiment, the junction location 26 is approximately 8 inches from the distal end 14 of the introducer sheath.

At the junction location 26, the auxiliary lumen 24 terminates. At the junction location 26, the main lumen 22 and the auxiliary lumen 24 join together and communicate with each other. Preferably, the auxiliary lumen 24 merges into the main lumen 22 in an tapering, inclined connection that forms a communicating port 30 between the main and the auxiliary lumens. The main lumen 22 extends distally from the junction location 26, as shown in FIG. 2b. The main lumen 22 terminates in a distal lumen opening 32 at the distal end 14 of the introducer sheath.

One or more markers 33 may be located at or proximate to the distal end 14. These markers may be formed of a radiopaque material such as platinum, gold, tungsten, iridium, alloys thereof. The markers 33 may be imbedded in the material forming the distal portion of the introducer sheath or may be attached by an adhesive or mechanical connection or other means. The markers serve to enable a physician to determine the position of the introducer sheath when it is in the patient's body by well known radioscopic means.

The introducer sheath may be used as follows: The introducer sheath 10 is positioned in the vascular system of a patient in a manner as is known in the art. The distal end 14 of the introducer sheath 10 is positioned close to the location of interest in the vascular system. This location may be an area that the physician may want to image by means of an ultrasonic imaging device. Alternatively, it may be an area where the physician may want to position a balloon device or an atherectomy device for the purpose of reducing or removing a stenosis. The proximal end 12 of the introducer sheath remains positioned outside the patient's body. A guide wire is positioned in the auxiliary lumen 24. The guide wire may be positioned in the auxiliary lumen 24 either before the introducer sheath is inserted into the patient's body or afterwards. The guide wire may be used to facilitate positioning of the introducer sheath. To use the guide wire for this purpose, the guide wire is extended through the communicating port 30 from the auxiliary lumen 24 into the main lumen 22 and out the distal lumen opening 32 past the distal end 12. In this position, the guide wire may be used to pass narrow or tortuous vessel regions that could be difficult or impossible for the introducer sheath to traverse by itself. The guide wire may have a formable or steerable tip located on the distal end thereof to facilitate traversing vessel regions. Once the guide wire is positioned as desired, the introducer sheath may be moved distally on the guide wire into its desired position. After the introducer sheath is in the desired position, the guide wire is withdrawn proximally into the auxiliary lumen 24. Because the communicating port 30 between the main and the auxiliary lumens is preferably inclined, withdrawal of the guide wire is facilitated. The therapeutic or imaging device is positioned, or has been positioned, in the main lumen 22 with the distal end of the device proximal of the communicating port 30. After the guide wire is withdrawn into the auxiliary lumen 24, the device can be extended distally past the communicating port 30, past the distal main lumen opening 32, and into the desired vessel region.

This embodiment of the introducer sheath has the advantage that if repositioning of the introducer sheath is required, such as due to a need to reposition the therapeutic or diagnostic device, the device need not be totally withdrawn. Further, the guide wire can readily be positioned near the distal end of the introducer sheath in the auxiliary lumen. For example, if repositioning of the therapeutic or diagnostic device is required, first the device is withdrawn into the main lumen 22 proximal of the communicating port 30. Then, the guide wire is extended from its position in the auxiliary lumen 2, past the communicating port 30, into the main lumen 22, and out the main distal lumen opening 32 into the patient's vessel. The guide wire may then be used to facilitate repositioning the introducer sheath.

After the introducer sheath has been repositioned as desired, the guide wire is again withdrawn into the auxiliary lumen 24 and the device extended again past the communicating port 30, past the main lumen distal opening 32, into the patient's vessel. Thus, with the present embodiment, the guide wire can be readily at hand to facilitate repositioning of the introducer sheath and need not be withdrawn entirely when other devices are used in the introducer sheath.

This embodiment of the introducer sheath provides the advantage that it includes two or more lumens at a proximal end and throughout most of its length to accommodate two or more devices, such as a therapeutic or diagnostic device in one lumen and, in another lumen, a guide wire used to facilitate positioning the device. In portions of the patient's vessel corresponding to this proximal portion of the introducer sheath, the vessel size is likely to be relatively large. Therefore, minimizing the overall exterior size of the introducer sheath is not essential and the vessel can likely readily accommodate the dual lumen proximal portion of the introducer sheath. However, at the distal portion of the introducer sheath, where the exterior dimensions of the introducer sheath are critical and ultimately define the vessel size limit of the device, the introducer sheath has only a single lumen. Thus, with the present embodiment, therapeutic and diagnostic devices can be positioned in distal regions of a patient's vascular system.

Although the above described embodiment of the present invention has been described in terms of using a guide wire in one lumen and a therapeutic or diagnostic device another lumen, the present embodiment should be construed to include other variations and uses. For example, a therapeutic device can occupy one lumen and a diagnostic device can occupy another. The diagnostic device may be an ultrasonic imaging device used to obtain ultrasonic images of the patient's vessel walls. After the images are obtained, the imager may be withdrawn and the therapeutic device, which may be an atherectomy device for example, may be extended from the distal end o the introducer sheath to remove the stenosis. Other combinations of devices are also contemplated within the scope of the invention.

The above described embodiment may also be used with more than two devices. For example, if a guide wire exchange is necessary, perhaps because a different size guide wire is considered necessary, the first guide wire may be totally withdrawn from the auxiliary lumen and a second guide wire inserted. Alternatively, the second guide wire may be installed into the main lumen if it is not otherwise occupied.

The above described embodiment has been described in terms of an introducer sheath with a main and an auxiliary lumen. In further embodiments, more than two lumens may be provided, consistent with any limitations on the overall exterior dimensions of the introducer sheath.

The introducer sheath may be made of an extruded polymeric material. Polyethylene is the preferred embodiment, however either polyurethane or PTFE Teflon also provide favorable construction. Use of a polyurethane is enhanced by applying a coating to the inner and outer surfaces to enhance lubricity. Alternatively, the introducer sheath may be formed of an acoustically transparent material, such as TPX, so that ultrasound imaging may be performed through the sheath material. Ultrasonic imaging may alternatively be performed by extending an imaging probe out of the distal end of the introducer catheter.

The dual lumen configuration of the introducer sheath may be formed in a single extrusion process. Alternatively, two individual tubes may be joined together by an adhesive joint or a thermal process. A single extrusion, dual-lumen tubing is the preferred embodiment.

In one alternative method of construction, the introducer sheath is made by starting with a dual lumen tubing and removing one of the lumens in a distal portion thereof. This may be done by slicing off one of the lumens by a cutting apparatus. Alternatively, a distal end of the dual lumen tubing may drawn through a heated die to reform the two lumens into one at the distal portion. During this reforming process, the walls may be thinned in the distal portion to make the introducer sheath more flexible in the distal portion.

Referring to FIGS. 3 and 4, there is shown another embodiment of the present invention. This embodiment includes a positioning member 40. The positioning member 40 is slidably located in a lumen of an introducer sheath which may be similar or identical to the introducer sheath of the above described embodiment of the invention. Accordingly, like numerals will be used in reference to the introducer sheath in this embodiment of the invention.

The positioning member 40 is located in the introducer sheath 10 in the lumen thereof that extends to the distal end 14 of the introducer sheath. In this embodiment, this lumen is the main or first lumen 22. The positioning member 40 includes a holding member 42 sized and adapted to be slidably positioned in the main lumen 22. The holding member 42 preferably has a cylindrical shape that tapers toward a distal end thereof. The holding member 42 has an outside diameter that is somewhat less than the inner diameter of the main lumen so that it can be readily moved proximally and distally in the main lumen 22 by sliding back and forth. The holding member 42 is tapered toward the distal end 44 to facilitate movement in a distal direction in the main lumen 22. The holding member 42 itself also includes an inner lumen 46 that extends through the holding member 42. The inner lumen 46 has a proximal opening 48 and a distal opening 50.

Connected to a proximal side of the holding member 42 adjacent to the proximal opening 48 of the inner lumen 46 is a proximal positioning wire 52. The positioning wire 52 forms an elongate rearward extension of the positioning member 40. The positioning wire 52 may be a wire made of metal or may be another elongate member. The 52 connects to the holding member 42 and extends proximately through the main lumen 22 and out the proximal end of the introducer sheath. The proximal end of the proximal positioning wire 52 may be used to move the holding member 42 proximally and distally so that the positioning member can be slidably positioned in the main lumen 22. The positioning member 40 can accommodate a device, such as guide wire, through the lumen 46 of the holding member 42. The guide wire may have very small diameter, such as 0.010 inches, in order to traverse vessel passages of correspondingly small diameter. The positioning member 40 is used to facilitate holding and positioning a device, such as a guide wire, that may have a diameter substantially smaller than the inner diameter of the main lumen 22. The guide wire is positioned in the lumen 46 of the holding member 42. This may be done external to the introducer sheath, if desired. Then the holding member 42 with the guide wire installed through it is inserted into the main lumen 22 of the introducer sheath. The holding member 42 with the included guide wire is advanced distally in the main lumen 22 of the introducer sheath by manually advancing the proximal end of the positioning wire 52. The holding member 42 may be advanced past the communicating port 30 of the introducer sheath to a location just proximal of the main lumen distal opening 32. The guide wire may be extended distally from that point by advancing the guide wire distally with respect to the positioning member 40. This may be accomplished manually from the proximal end as well. By means of the positioning member 40, a guide wire may be used with the introducer sheath in a lumen thereof. Alternatively, devices other than a guide wire may be positioned by means of the positioning member 40. Such devices include balloon catheters, atherectomy devices, imagers, and so on.

Referring to FIGS. 5 to 8, there are shown alternative embodiments of the present invention. These alternative embodiments represent different lumen configurations and geometries for the proximal (dual lumen portion) of the introducer sheath. These alternative embodiments may provide specific manufacturing or operational advantages.

Included in the table below are presently preferred alternative dimensions for the embodiments of FIGS. 5 to 8.

| Config. | Desc. | Dim A | Dim B | Dim C | Dim D | Dim E |
|---|---|---|---|---|---|---|
| 1 | .014 GW | .004 | .004 | .018 | .035 | .065 |
| 2 | " | " | " | " | .040 | .070 |
| 3 | " | " | " | " | .045 | .075 |
| 4 | " | " | " | " | .050 | .080 |
| 5 | .018 GW | .005 | .005 | .021 | .035 | .071 |
| 6 | " | " | " | " | .040 | .076 |
| 7 | " | " | " | " | .045 | .081 |
| 8 | " | " | " | " | .050 | .086 |

Figure 9:
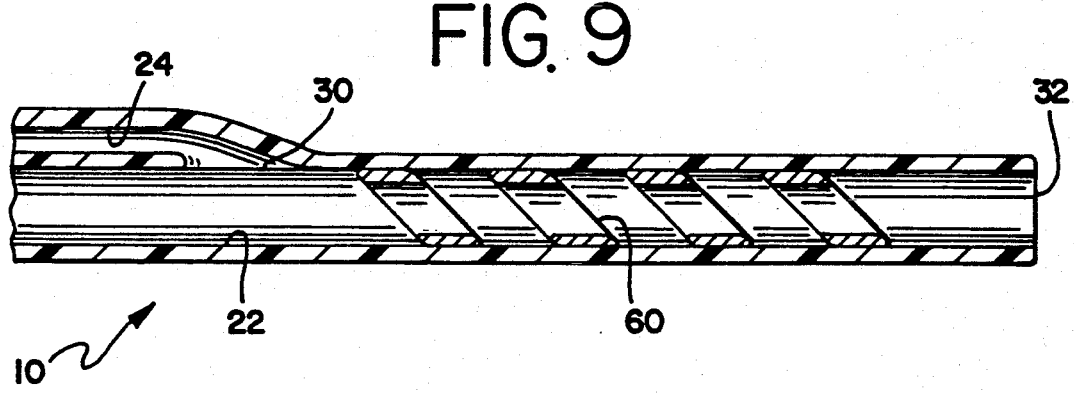
FIG. 9 shows a longitudinal cross section of another alternative embodiment.

Referring to FIG. 9, there is depicted another alternative embodiment of the present invention. In this embodiment, there is included a support member 60 located in the distal portion of the introducer sheath. The support member 60 may preferably be formed of a coil of a flat metal wire stock. The support member 60 may be formed of gold, platinum, tungsten iridium or alloys thereof to provide for radiopacity, if desired. The support member 60 may alternatively be in the form of a braid or other configuration. The support member 60 may be located on the interior of the sheath in the main lumen 22 at a distal portion thereof to provide for resistance to collapse or to provide for radiopacity. Alternatively, the support member 60 may be located on the exterior of the sheath and bonded or otherwise connected thereto.

Referring to FIGS. 10 and 11, there is depicted another embodiment of the present invention. In this embodiment, an introducer sheath 70 is provided formed of material(s) and with dimensions similar or identical to the introducer sheath 10, described above. The introducer sheath 70 has a first or main lumen 72 and a second or auxiliary lumen 74 communicating with ports 76 and 78, respectively, of a manifold 80. The auxiliary lumen 74 terminates at and communicates with the main lumen 72 at a location 82 which is proximal of a distal end 84 of the introducer sheath 70 at which the main lumen 72 terminates in a main lumen distal opening 86.

In this embodiment of the present invention, one or more openings 88 are located in the introducer sheath 10 proximal of the location 82. The openings 88 allow the introducer sheath 70 to provide for perfusion during use when positioned intravascularly. The openings 88 extend through a portion of the introducer sheath wall so that the interior and the exterior of the introducer sheath 70 may be in fluid communication In a preferred embodiment, the one or more holes 88 are located in the portion of the introducer sheath 70 corresponding to the wall of the auxiliary lumen 74 so that the auxiliary lumen interior is in fluid communication with the exterior of the introducer sheath 70. Alternatively, the one or more openings 88 may be located in a portion of the introducer sheath corresponding to the main lumen 72 or in portions of the introducer sheath corresponding to both the main and auxiliary lumens. The one or more openings 88 may include 6 openings, or alternatively more or less than 6 openings may be provided. Each opening may be approximately 0.010 inches in diameter and extend through the introducer sheath wall either perpendicularly or at an angle to a normal axial direction. If more than one opening is provided, the openings may be spaced from each other by approximately 0.25 inches or may be spaced from each other by other distances either regularly or irregularly. Also, the opening 88 may be aligned along the introducer sheath in a straight line or may be provided in a staggered or other arrangement. In one embodiment, the openings 88 are located in the auxiliary lumen wall beginning at a location approximately ½ inch proximally from the communication location 82 and extending proximally therefrom.

An exemplary method for using the introducer sheath 70 is described as follows: The introducer sheath 70 may be used in conjunction with an angioplasty procedure in which a balloon dilation catheter is positioned across a region of a person's vascular system narrowed by arthersclerotic disease, e.g, a stenosis. The location at which the vessel narrowing occurs may be determined by angiographic methods known in the art, or by other methods such as ultrasound, optical fiber, etc. According to this embodiment, the introducer sheath 70 is positioned in the vascular system of the patient in a manner like the embodiments described above. A guide wire (not shown) is installed into the vascular system via the auxiliary lumen 74. A balloon dilation catheter of the fixed wire type is installed in the main lumen 72 so that a distal end of the dilation catheter is proximal of the location 82. The balloon catheter may be an ACE catheter manufactured by SciMed Life Systems, Inc. of Maple Grove, Minn. The introducer sheath 70 is advanced so that the distal end 84 of the introducer sheath is proximal of the site of the stenosis. The guide wire is extended out the distal end of the introducer sheath 70 and an attempt is made to cross the diseased region. If successful, the introducer sheath 70 is advanced distally over the guide wire so that the distal end is across the stenosis. Then, the guide wire is withdrawn proximally so that a proximal end is proximal of the location 82. Then, the dilation catheter is advanced so that the balloon is across the stenosis and the introducer sheath is withdrawn slightly so that the balloon portion of the dilation catheter is at the narrowed site. Dilation is attempted according to known techniques. If it is determined that a different dilation catheter is needed, e.g. with a different size balloon for example, the introducer sheath is advanced over the first dilation catheter and across the stenosis. Then, the first dilation catheter is withdrawn. The guide wire is moved proximally several inches in the auxiliary lumen 74 so that at least some of the openings 88 are distal of the distal end of the guide wire. Blood can then perfuse through the introducer sheath 70 via the openings 88, the distal portion of the auxiliary lumen 74, the distal portion of the main lumen 72 and the distal opening 86 of the main lumen 72. This allows blood to perfuse across the stenosis while a second dilation catheter is prepped and installed into the main lumen 72. Then, the second dilation catheter is advanced through the main lumen 72 and out the distal end 84 of the introducer sheath 70 so that the balloon of the second dilation catheter is positioned across the stenosis. Dilation is then attempted with the second balloon catheter.

It can readily be appreciated that there are various alternatives methods of use. For example, instead of exchanging a first dilation balloon catheter for another dilation balloon catheter, it may be indicated after a balloon angioplasty that an atherectomy device is needed, e.g. to treat or remove loose tissue. The introducer sheath 70 can be installed across the site to allow blood perfusion while the atherectomy device is prepared and installed. An advantage of the present embodiment is that not only can a secure path for blood perfusion be maintained across a vessel site, but also multiple paths for guide wires, balloon catheter, atherectomy devices, imaging devices, etc. can also be maintained across the site.

Referring to FIGS. 12 and 13, there is depicted another embodiment of the present invention. In this embodiment, an introducer sheath 100 is provided formed of material(s) and with dimensions similar or identical to introducer sheaths 10 and 70, described above. The introducer sheath 100 has a first or main lumen 102 and a second or auxiliary lumen 104. The first lumen 102 communicates proximally with a port 106 of a manifold 110. The main lumen 102 terminates distally in a main lumen distal opening 112. An auxiliary lumen 104 terminates distally at and communicates with the main lumen 102 at a location 114 which is proximal of a distal end 116 of the introducer sheath 100.

In this embodiment 100, the auxiliary lumen 104 extends proximally from the location 114 and terminates at an opening 117 at a location 118 distal of a proximal end 120 of the introducer sheath 100. (In addition, in this embodiment 100 of the introducer sheath, one or more openings 119 may be provided in a portion of the wall of the introducer sheath 100 proximal of the location 114 to provide for perfusion as in the embodiment depicted in FIGS. 10 and 11). The length of the auxiliary lumen 104, i.e. the distance between the locations 114 and 118, may be any length, but in one embodiment the length is approximately 4 inches.

This embodiment of the introducer sheath 100 allows for quick exchange of one introducer sheath for another. Because the auxiliary lumen 104 terminates at a location near the distal end 116 of the introducer sheath 100, the introducer sheath 100 can be exchanged for another intravascular device, such as another balloon catheter, or even another introducer sheath perhaps of a different size, over a positioning guide wire extending through the auxiliary lumen 104 and out the end 116 of the sheath while leaving the guide wire in place in the vessel with a distal end across the site.

An exemplary method for using the introducer sheath 100 is described as follows: The introducer sheath 100 may be used in conjunction with an angioplasty procedure in which a balloon dilation catheter is positioned across a region of a person's vascular system narrowed by arthersclerotic disease, e.g, a stenosis. The location at which the vessel narrowing occurs may be determined by angiographic methods known in the art, or by other methods such as ultrasound, optical fiber, etc. According to this embodiment, a first guide wire (not shown) is installed in the main lumen 102 and a second guide wire is installed into the auxiliary lumen 104. The first guide wire may be a conventional guide wire used for positioning and the second guide wire may be an imaging guide wire that is used scan the vasculature with ultrasound to produce images of the vessel geometry. (An imaging guide wire of the type considered herein is disclosed in copending application Ser. No. 07/668,919, filed Mar. 13, 1991, the disclosure of which is incorporated herein by reference). The introducer sheath 100 is positioned in the vascular system of the patient in a manner like the embodiments described above. An attempt is made to cross the lesion with the first guide wire. If successful, the introducer sheath may be advanced over the lesion, the first guide wire withdrawn entirely into the auxiliary lumen 104 and the imaging guide wire advanced to obtain images of the vessel geometry. However, it may occur that the introducer sheath 100 is too large to cross the lesion and therefore an introducer sheath of a different size is required. With the present embodiment, a first introducer sheath can be readily exchanged for another introducer sheath without withdrawing the first guide wire from its position across the lesion. In such a circumstance, the first guide wire is left in place across the lesion and the introducer sheath 100 is withdrawn thereover. Then, another introducer sheath having different dimensions is advanced over the same first positioning guide wire and another attempt is made to cross the stenosis.

(If it becomes necessary to exchange a guide wire in the auxiliary lumen 104 of the embodiment of FIGS. 12 and 13, this can be accomplished by means of a guide wire sheath as disclosed in copending application Ser. No. 07/725,064 filed Jul. 5, 1991, the disclosure of which is incorporated herein by reference).

Figure 14:
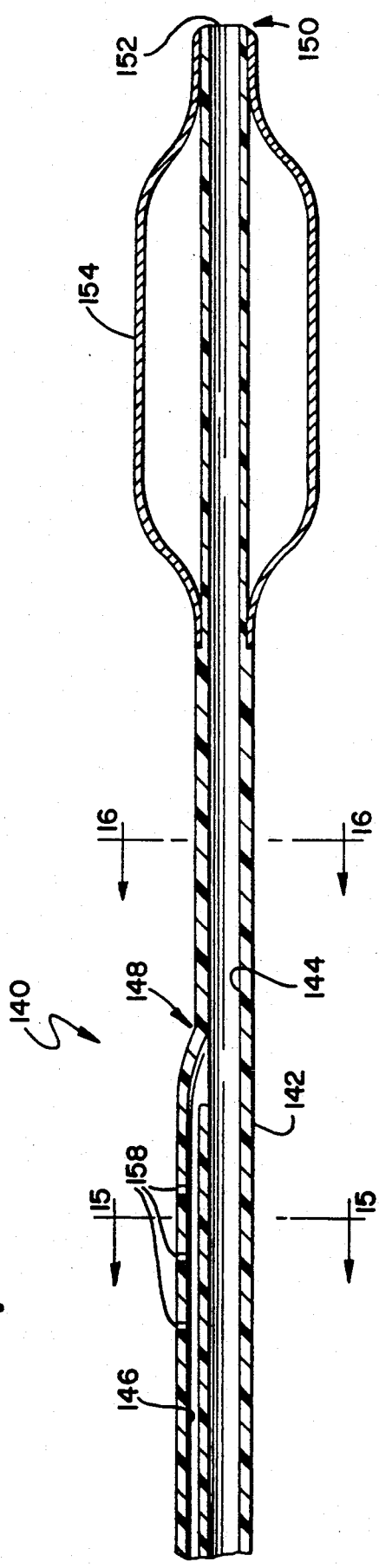
FIG. 14 shows another embodiment of the present invention.
Figure 16:
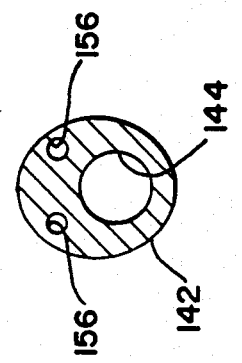
FIG. 16 is a cross section corresponding to line 16—16' of FIG. 14
Figure 15:
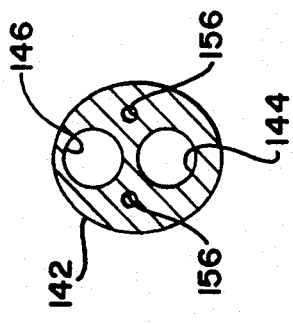
FIG. 15 is a cross section corresponding to line 15—15' of FIG. 14.

Referring to FIGS. 14–16, there is depicted another embodiment of the present invention. In this embodiment, a multi-guide wire lumen design is incorporated into a balloon catheter 140. The balloon catheter 140 may be formed of material(s) and with dimensions similar or identical to commercially available balloon catheters such as the Skinny or MVP manufactured by Scimed Life Systems of Maple Grove, Minn., except that instead of a single guide wire lumen extending through the shaft and balloon, the balloon catheter 140 includes an elongate shaft 142 having a first or main lumen 144 and a second or auxiliary lumen 146 communicating with ports of a proximally located manifold (not shown). The auxiliary lumen 146 terminates at and communicates with the main lumen 144 at a location 148 which is proximal of a distal end 150 of the balloon catheter 140. The main lumen 144 terminates in a main lumen distal opening 152 at the distal end 150. In this embodiment, an inflatable balloon 154 is located on a distal portion of the elongate shaft 142. One or more inflation lumens 156 extend through the elongate shaft 142 and communicate with the interior of the balloon 154. Inflation fluid is conveyed by the path formed by the one or more inflation lumens 154 to inflate and deflate the balloon in 154 a manner that is known in the art for the purposes of dilating narrowed vessels of the body.

This multi-lumen dilation balloon catheter 140 of this embodiment may be provided, in alternative embodiments, with features of the other embodiments, such as perfusion openings 158 located in a portion of the elongate member 142 proximal of the balloon 154 or proximal of the location 148 at which the main and the auxiliary lumens communicate.

A method for using the present embodiment 140 is as follows: A first guide wire is positioned in the main lumen 144 and a second guide wire is positioned in the auxiliary lumen 146. The first wire may be of a conventional type used for positioning over-the-wire and single-operator-exchange type catheters. The second guide wire may be of an imaging type, as disclosed in copending application Ser. No. 07/704,828, filed May 23, 1991, the disclosure of which is incorporated herein by reference. The imaging guide wire includes an ultrasonic transducer located at the distal portion adapted to scan the vasculature to obtain images thereof. The balloon catheter 140 is positioned in the vascular system of a patient in a manner that is known in the art. This may typically involve an incision into the body of the patient in the groin to provide access to the femoral artery. Typically, a short introducer sheath (not to be confused with the long multi-lumen introducer sheath described elsewhere in this specification) is positioned in the artery and a guide catheter installed therein to provide access to the ostium. The balloon catheter 140 and the first and second guide wires are advanced to the coronary site at which treatment is to take place. The first guide wire is used to position the balloon catheter and may possess characteristics that allow it to cross tortuous portions of the vasculature. Once the first guide wire is positioned across the lesion or stenosis, the balloon catheter 140 may be advanced over it in a usual manner so that the balloon portion 154 is at the vessel treatment site. Then, the first guide wire is withdrawn proximal of the location 148 and the imaging guide wire is advanced so that it can scan the vasculature through the catheter 140. (In order to do this, the catheter 140 can be provided so that at least a portion thereof is formed of a material that is ultrasonically transparent, such as TPX). This imaging can be useful to the physician to diagnose the extent of the lesion. The imaging may be used in conjunction with other diagnostic techniques such as angiographic dyes. If the physician is satisfied with the information obtained, the dilation may take place in the usual manner. Then, after deflation, ultrasonic images may be obtained again to observe the efficacy of treatment. Additional dilations or other therapy may be indicated if the physician is not satisfied with the results observed. Such additional therapies may be initiated while a path across the vessel narrowing site is available thereby facilitating such additional procedures.

It can readily be appreciated that there are numerous alternative methods taking advantage of the multiple guide wire lumens of this embodiment. For example, both the first and the second guide wires can be for positioning but with different characteristics. For instance, one guide wire can be relatively flexible and the other can be relatively stiff. If the physician considers that both may be needed, possibly alternatively, both the guide wires can be ready and in the balloon catheter ready for use. The guide wire can be alternatively retracted and extended as needed.

Referring to FIGS. 17-20, there is depicted another embodiment of the present invention. In this embodiment, a multi-guide wire lumen design is incorporated into a balloon catheter 160. As in the previously described embodiments, the balloon catheter 160 may be formed of material(s) and with dimensions similar or identical to commercially available balloon catheters. The balloon catheter 160 differs from the balloon catheter 140 shown in FIGS. 14-16 in that one of the wire lumens terminates at a location distal of the proximal end of the catheter. The balloon catheter 160 includes an elongate shaft 162 having a first or main lumen 164 and a second or auxiliary lumen 166. The main lumen 164 communicates with a port of a proximally located manifold (not shown). The auxiliary lumen 166 terminates distally at and communicates with the main lumen 164 at a location 168 which is proximal of a distal end 170 of the balloon catheter 160. The main lumen 164 terminates in a main lumen distal opening 172 at the distal end 170. An inflatable balloon 174 is located on a distal portion of the elongate shaft 162. One or more inflation lumens 176 extend through the elongate shaft and communicate with the interior of the balloon 174. Inflation fluid is conveyed by the path formed by the one or more inflation lumens 176. This multi-lumen inflation balloon of the present embodiment may be provided with perfusion openings 178 located in a portion of the elongate member proximal of the balloon or proximal of the location at which the main and the auxiliary lumen communicate. In this embodiment, the auxiliary lumen 66 terminates at a location 180 so that the auxiliary lumen 166 is relatively short, e.g. 4-6 -inches.

The relatively short auxiliary lumen 166 enables a physician to facilitate a quick exchange of this balloon catheter with another, for example, if a balloon of different dimensions is required. Such an exchange can be performed in a manner as is done now with balloon catheters such as described above with respect to the embodiment shown in FIGS. 12 and 13. Accordingly, an exemplary method of operating the balloon catheter 160 would be as follows: A guide wire is positioned in the auxiliary lumen 166 and the guide wire and the balloon catheter 160 are advanced through a guide catheter intravascularly. An attempt is made to cross the stenosis with the guide wire. If the guide wire can be successfully positioned across the stenosis, the catheter 160 is advanced over the guide wire and across the stenosis. Then, the guide wire is withdrawn so that the distal end of the guide wire is proximal of the location 168. Then, an imaging guide wire is advanced through the main lumen 164. The imaging guide wire is advanced out the distal opening 172. Then, the catheter is withdrawn slightly so that the imaging guide wire can make ultrasonic scans of the vasculature at the site of the stenosis. (Alternatively, the imaging guide wire can scan through the catheter 160 if at least a portion of the catheter, e.g. a window, is formed of an ultrasonically transparent material). Then, the catheter 160 is advanced over the imaging guide wire and the balloon 174 is inflated to dilate the vessel at the site. If a catheter of a different size or a catheter of a different type, e.g. an atherectomy device, is indicated, the balloon catheter 160 can be exchanged for the other catheter device by first withdrawing the imaging guide wire proximally of the location 168, advancing the positioning guide wire out the distal end 170 and across the stenosis, and exchanging the catheter 160 for the other device over the first (positioning) guide wire.

It is intended that the foregoing detailed description be regarded as illustrated rather than limiting and that it is understood that the following claims including all equivalents are intended to define the scope of the invention.

We claim:

1. An intravascular device comprising an elongate member having a proximal end and a distal end with a first proximal opening at the proximal end of the elongate member communicating with a first lumen located therein, a first distal opening at the distal end of the elongate member communicating with the first lumen, and second proximal opening at the proximal end of the elongate member communicating with a second lumen located therein, a distal end of the second lumen terminating and communicating with the first lumen at a location therein proximal of the first distal opening, said elongate member having one or more perfusion openings located in a wall forming the elongate member to provide a fluid path between the exterior of the elongate member and at least one said first and said second lumens.

2. The intravascular device of claim 1 in which the one or more openings are located in a portion of the wall of the elongate member proximal of the location at wall of the elongate member corresponding to the second lumen.

3. The intravascular device of claim 1 in which the one or more openings are located in a portion of the wall of the elongate member corresponding t the second lumen.

4. The intravascular device of claim 1 in which said second lumen terminates at a location distal of the proximal end of the first lumen.

5. The intravascular device of claim 4 in which said second lumen terminates proximally at a location normally positioned inside a persons' vessel during use.

6. The intravascular device of claim 1 further including an inflatable balloon connected to a distal portion of the elongate member and in which said elongate member further includes at least one inflation lumen communicating with the interior of the balloon and extending to the proximal end of the elongate member whereby the intravascular device can used to perform an angioplasty procedure and can be positioned in a vessel of a body over a guide wire located in at least one of the first and the second lumens.

7. The intravascular device of claim 1 in which said elongate member comprises an introducer sheath.

8. An intravascular device comprising an elongate member having a proximal end connected to said manifold and a distal end with a first proximal opening at the proximal end of the elongate member communicating with a first lumen located therein, a first distal opening at the distal end of the elongate member communicating with the first lumen, and a second lumen located in the elongate member, a distal end of the second lumen terminating distally and communicating with the first lumen at a location therein proximal of the first distal opening, and further in which said second lumen terminates proximally at a location distal of the proximal end of the first lumen and said manifold.

9. The intravascular device of claim 8 further comprising:

an inflatable balloon connected to a distal portion of the elongate member and in which said elongate member further includes at least one inflation lumen communicating with the interior of the balloon and extending to the proximal end of the elongate member whereby the intravascular device can used to perform an angioplasty procedure and can be positioned in a vessel of a body over a guide wire located in at least one of the first and the second lumens.

10. The intravascular device of claim 8 in which said elongate member comprises an introducer sheath.

11. The intravascular device of claim 8 in which said second lumen terminates proximally at a location normally positioned inside a persons' vessel during use.

12. A balloon catheter comprising:

an elongate shaft having a distal portion and a proximal portion, said distal portion adapted to be positioned intravascularly in the body of a patient and a proximal portion adapted to be located outside the body;

said elongate member further having a first proximal opening at a proximal end of the elongate member communicating with a first lumen located therein, a first distal opening at a distal end of the elongate member communicating with the first lumen, and second proximal opening at the proximal end communicating with a second lumen, a distal end of the second lumen terminating and communicating with the first lumen at a location therein proximal of the first distal opening, and an inflatable balloon connected to the distal portion of the elongate member, said balloon in fluid communication with the proximal portion of the elongate member by an inflation lumen extending through the elongate member.

13. The balloon catheter of claim 12 in which said elongate member has one or more perfusion openings located in a wall forming the elongate member in a location therein proximal of the balloon.

14. The balloon catheter of claim 13 in which said one or more perfusion openings are located proximal of the location at which said second lumen communicates with the first lumen.

15. The balloon catheter of claim 14 in which the one or more openings are located in a portion of the wall of the elongate member corresponding to the second lumen.

16. The balloon catheter of claim 13 in which said second lumen terminates at a location distal of the proximal end of the first lumen.

17. The balloon catheter of claim 12 in which said second lumen terminates at a location distal of the proximal end of the first lumen.

18. A method for using an intravascular device, the intravascular device including an elongate member having a proximal end and a distal end with a first proximal opening at the proximal end of the elongate member communicating with a first lumen located therein, a distal opening at the distal end of the elongate member communicating with the first lumen, and second proximal opening at the proximal end of the elongate member communicating with a second lumen located therein, a distal end of the second lumen terminating and communicating with the first lumen at a location therein proximal of the distal opening, said elongate member having one or more perfusion openings located in a wall forming the elongate member in a location therein proximal of the location at which said second lumen communicates with the first lumen, said method comprising the steps of:
   advancing the intravascular device into a vessel of a patient so that the distal portion is across a site in the vessel;
   maintaining the device in the vessel so that blood can perfuse through the perfusion openings and the distal opening.

19. The method of claim 18 further comprising the steps of:
   advancing a guide wire through at least one of the first and the second lumen; withdrawing the guide wire proximally of at least the location at which the second lumen communicates with the first lumen.

20. The method of claim 18 further comprising the step of: exchanging the first intravascular device for another intravascular device.

21. The method of claim 20 in which the second lumen of the intravascular device terminates proximally in an opening distal of the proximal end of the device and in which the step of exchanging further comprises:
   withdrawing the intravascular device over a guide wire extending into the second lumen.

22. The method of claim 18 in which the intravascular device comprises an introducer sheath.

23. The method of claim 18 in which the intravascular device comprises a balloon catheter.

24. The method of claim 18 further comprising the step of:
   advancing an imaging guide wire through at least one of said lumens, and
   ultrasonically scanning the vasculature of the person from within.

25. A method for using an intravascular device, the intravascular device comprising a manifold and an elongate member having a proximal end connected to said manifold and a distal end with a first proximal opening at the proximal end of the elongate member communicating with a first lumen located therein, a first distal opening at the distal end of the elongate member communicating with the first lumen, and a second lumen located in the elongate member, a distal end of the second lumen terminating distally and communicating with the first lumen at a location therein proximal of the first distal opening, and further in which said second lumen terminates proximally at a location distal of the proximal end of the first lumen and said manifold, said method comprising the steps of:
   advancing the intravascular device into a vessel of a patient so that the distal portion is across a site in the vessel;
   exchanging the first intravascular device for another intravascular device.

26. The method of claim 25 further comprising the step of:
   withdrawing the intravascular device over a guide wire extending into the second lumen.

27. The method of claim 25 in which the intravascular device comprises an introducer sheath.

28. The method of claim 25 in which the intravascular device comprises a balloon catheter.

29. The method of claim 24 further comprising the step of:
   advancing an imaging guide wire through at least one of said lumens, and
   ultrasonically scanning the vasculature of the person from within.

* * * * *

Disclaimer 5,219,335 - Lloyd Willard, Miltona; Wayne Sieben, Alexandria, both of Minn. INTRAVASCULAR DEVICE SUCH AS INTRODUCER SHEATH OR BALLOON CATHETER OR THE LIKE AND METHODS FOR USE THEREOF. Patent dated June 15, 1993. Disclaimer filed May 3, 1999, by the assignee, Scimed Life Systems, Inc.

Hereby enters this disclaimer to claims 1-5, 7, 8, 10, 11, 18-22, 24-27 and 29 of said patent.
*(Official Gazette, June 22, 1999)*